(12) United States Patent
Case

(10) Patent No.: US 7,794,504 B2
(45) Date of Patent: Sep. 14, 2010

(54) METHOD FOR MAKING A METAL-BACKED ACETABULAR IMPLANT

(75) Inventor: Kirt L. Case, Warsaw, IN (US)

(73) Assignee: Zimmer Technology, Inc., Warsaw, IN (US)

( * ) Notice: Subject to any disclaimer, the term of this patent is extended or adjusted under 35 U.S.C. 154(b) by 0 days.

(21) Appl. No.: 12/331,073

(22) Filed: Dec. 9, 2008

(65) Prior Publication Data

US 2009/0088866 A1 Apr. 2, 2009

Related U.S. Application Data

(63) Continuation of application No. 11/104,974, filed on Apr. 12, 2005, now abandoned.

(51) Int. Cl.
*A61F 2/32* (2006.01)
(52) U.S. Cl. .............. 623/22.21; 623/22.11; 623/22.24
(58) Field of Classification Search ............. 623/22.11, 623/22.15, 22.17, 22.18, 22.21, 22.23, 22.24, 623/22.25
See application file for complete search history.

(56) References Cited

U.S. PATENT DOCUMENTS 2,900,272 A 8/1959 Coleman, Jr. et al.

(Continued)

FOREIGN PATENT DOCUMENTS

EP 0065482 A1 11/1982

(Continued)

OTHER PUBLICATIONS

Office Action mailed Oct. 18, 2007 from U.S. Appl. No. 11/104,974.
Final Office Action mailed Jul. 10, 2008 from U.S. Appl. No. 11/104,974.

(Continued)

*Primary Examiner*—Alvin J Stewart
*Assistant Examiner*—Yashita Sharma
(74) *Attorney, Agent, or Firm*—Baker & Daniels LLP

(57) ABSTRACT

A metal-backed acetabular implant and a method of forming the same.

18 Claims, 8 Drawing Sheets

U.S. PATENT DOCUMENTS

| | | | |
|---|---|---|---|
| 3,683,421 A | 8/1972 | Martinie |
| 3,903,549 A | 9/1975 | Deyerle |
| 3,978,528 A | 9/1976 | Crep |
| 4,180,873 A | 1/1980 | Fixel |
| 4,624,674 A | 11/1986 | Pappas et al. |
| 4,642,123 A | 2/1987 | Noiles |
| 4,678,472 A | 7/1987 | Noiles |
| 4,770,658 A | 9/1988 | Geremakis |
| 4,795,470 A | 1/1989 | Goymann et al. |
| 4,813,963 A | 3/1989 | Hori et al. |
| 5,092,897 A | 3/1992 | Forte |
| 5,282,864 A | 2/1994 | Noiles et al. |
| 5,310,408 A | 5/1994 | Schryver et al. |
| 5,314,491 A | 5/1994 | Thongpreda et al. |
| 5,362,311 A | 11/1994 | Amino et al. |
| 5,383,938 A | 1/1995 | Rohr et al. |
| 5,507,824 A | 4/1996 | Lennox |
| 5,549,691 A | 8/1996 | Harwin |
| 5,549,701 A | 8/1996 | Mikhail |
| 5,593,445 A | 1/1997 | Waits |
| 5,725,591 A | 3/1998 | DeCarlo et al. |
| 5,824,108 A | 10/1998 | Huebner |
| 5,879,397 A | 3/1999 | Kalberer et al. |
| 5,938,698 A | 8/1999 | Sandoz |
| 5,989,294 A | 11/1999 | Marlow |
| 6,231,612 B1 | 5/2001 | Balay et al. |
| 6,328,764 B1 | 12/2001 | Mady |
| 6,352,559 B1 | 3/2002 | Church |
| 6,475,243 B1 | 11/2002 | Sheldon et al. |
| 6,527,808 B1 | 3/2003 | Albertorio et al. |
| 6,589,284 B1 | 7/2003 | Silberer |
| 6,610,097 B2 | 8/2003 | Serbousek et al. |
| 6,620,200 B1 | 9/2003 | Descamps et al. |
| 6,827,742 B2 | 12/2004 | Hayes et al. |
| 6,916,342 B2 | 7/2005 | Frederick et al. |
| 6,976,999 B2 | 12/2005 | Charlebois et al. |
| 7,115,145 B2 | 10/2006 | Richards |
| 7,208,222 B2 | 4/2007 | Rolf et al. |
| 2001/0037156 A1 | 11/2001 | Burstein et al. |
| 2003/0050703 A1 | 3/2003 | Harris et al. |
| 2003/0105529 A1 | 6/2003 | Synder et al. |
| 2003/0187512 A1 | 10/2003 | Frederick et al. |
| 2005/0004677 A1 | 1/2005 | Johnson |
| 2005/0004678 A1 | 1/2005 | Richards |
| 2005/0102034 A1 | 5/2005 | Hayes et al. |
| 2005/0240276 A1 | 10/2005 | Shea et al. |
| 2006/0241781 A1 | 10/2006 | Brown et al. |
| 2007/0106390 A1 | 5/2007 | Richards |
| 2007/0239283 A1 | 10/2007 | Newsome et al. |

FOREIGN PATENT DOCUMENTS

| | | |
|---|---|---|
| EP | 0066092 A1 | 12/1982 |
| EP | 0086879 A1 | 8/1983 |
| EP | 0190093 A1 | 8/1986 |
| EP | 0694294 A1 | 1/1996 |
| EP | 0773007 A1 | 5/1997 |
| FR | 2357235 A1 | 2/1978 |
| FR | 2519545 A1 | 7/1983 |
| FR | 2684544 A1 | 6/1993 |
| FR | 2824258 A1 | 11/2000 |
| FR | 2805151 A1 | 8/2001 |
| GB | 2306330 A | 1/2008 |
| WO | WO0064383 A1 | 11/2000 |

OTHER PUBLICATIONS

Webpage—Zimmer Product—Epsilon Durasul Constrained Insert, 3 pages, 2007 Zimmer, Inc.

Wright Medical Technology, Inc. "Lineage Acetabular Cup System Surgical Technique," copyright 2003, Arlington, TN 38002 (12 pages).

Office Action mailed Jun. 18, 2007, in U.S. Appl. No. 11/104,351.

Article The Balgrist Hip Socked for Cementless Fixation in Primary Total Hip Replacements and in Acetabular Revisions, Hauser et al., ACTA Chriurgiae Orthopaedicae et Traumatologiae Cechosl. 61, 1994.

Product Brochures—MetaSUL, AlloPro product line of Sulzer Orthopedics, Jan. 1997.

US 7,794,504 B2

METHOD FOR MAKING A METAL-BACKED ACETABULAR IMPLANT

CROSS REFERENCE TO RELATED APPLICATION

This application is a continuation of U.S. patent application Ser. No. 11/104,974, entitled "Method for Making a Metal-Backed Acetabular Implant," filed on Apr. 12, 2005 by the same inventor hereof, the disclosure of which is expressly incorporated herein by reference.

BACKGROUND

1. Field of the Invention

The present invention relates generally to the field of orthopaedics, and, more particularly, to a method of making a metal-backed acetabular implant for a hip prosthesis.

2. Description of the Related Art

A conventional hip prosthesis is primarily composed of an acetabular implant and a femoral implant. The acetabular implant typically includes a generally hemispherical dome-like or cup-like metallic shell secured within the acetabulum and a dome-like or cup-like plastic or ceramic bearing secured within the shell. Accordingly, the shell typically includes an exterior configured to be anchored into the acetabulum and further typically includes an interior configured to align and retain the bearing, while the bearing typically includes an exterior configured to cooperate with the interior of the shell to align and secure the bearing within the shell and further typically includes an interior defining an artificial hip socket (which may or may not be off-centered from the exterior of the bearing, depending on the particular design). The femoral implant typically includes an elongated metallic spike or post at one end and a metallic ball at the other. The post is typically configured to be anchored into the distal femoral medullary canal and the ball is typically configured to insert into the artificial socket. Pivotal freedom of the ball within the socket allows articulation of the prosthetic joint.

A substantial dislocation and/or rotation of the bearing relative to the shell can potentially degrade the biomechanics and/or wear characteristics of the conventional hip prosthesis. Historically, balancing the needs for effective bearing retention with competing desires for design simplicity and versatility has been challenging.

SUMMARY

The present invention provides a metal-backed acetabular implant and a method of forming the same.

According to an embodiment of the present invention, an acetabular implant is provided including a shell, an integument, and a plastic bearing. The shell has an outer shell surface configured to contact bone and an inner shell surface. The integument has an outer integument surface configured to couple to the inner shell surface and an inner integument surface. The plastic bearing has an outer bearing surface and an inner bearing surface defining a socket, the inner integument surface configured to form a friction-fit with the outer bearing surface.

According to another embodiment of the present invention, an acetabular implant is provided including a shell, a plastic bearing, and an integument. The shell is configured to contact bone. The plastic bearing defines a socket. The integument is positionable between the shell and the bearing, the integument configured to form a friction-fit with the bearing.

According to yet another embodiment of the present invention, a method is provided to form a metal-backed acetabular implant. The method includes the steps of providing a plastic bearing having an outer bearing surface and an inner bearing surface defining a socket; providing an integument having an outer integument surface and an inner integument surface; forming a sub-assembly by friction-fitting the outer bearing surface to the inner integument surface; providing a shell; and forming an implant by coupling the shell and the sub-assembly.

The above-noted features and advantages of the present invention, as well as additional features and advantages, will be readily apparent to those skilled in the art upon reference to the following detailed description and the accompanying drawings, which include a disclosure of the best mode of making and using the invention presently contemplated.

DETAILED DESCRIPTION

Figure 1:
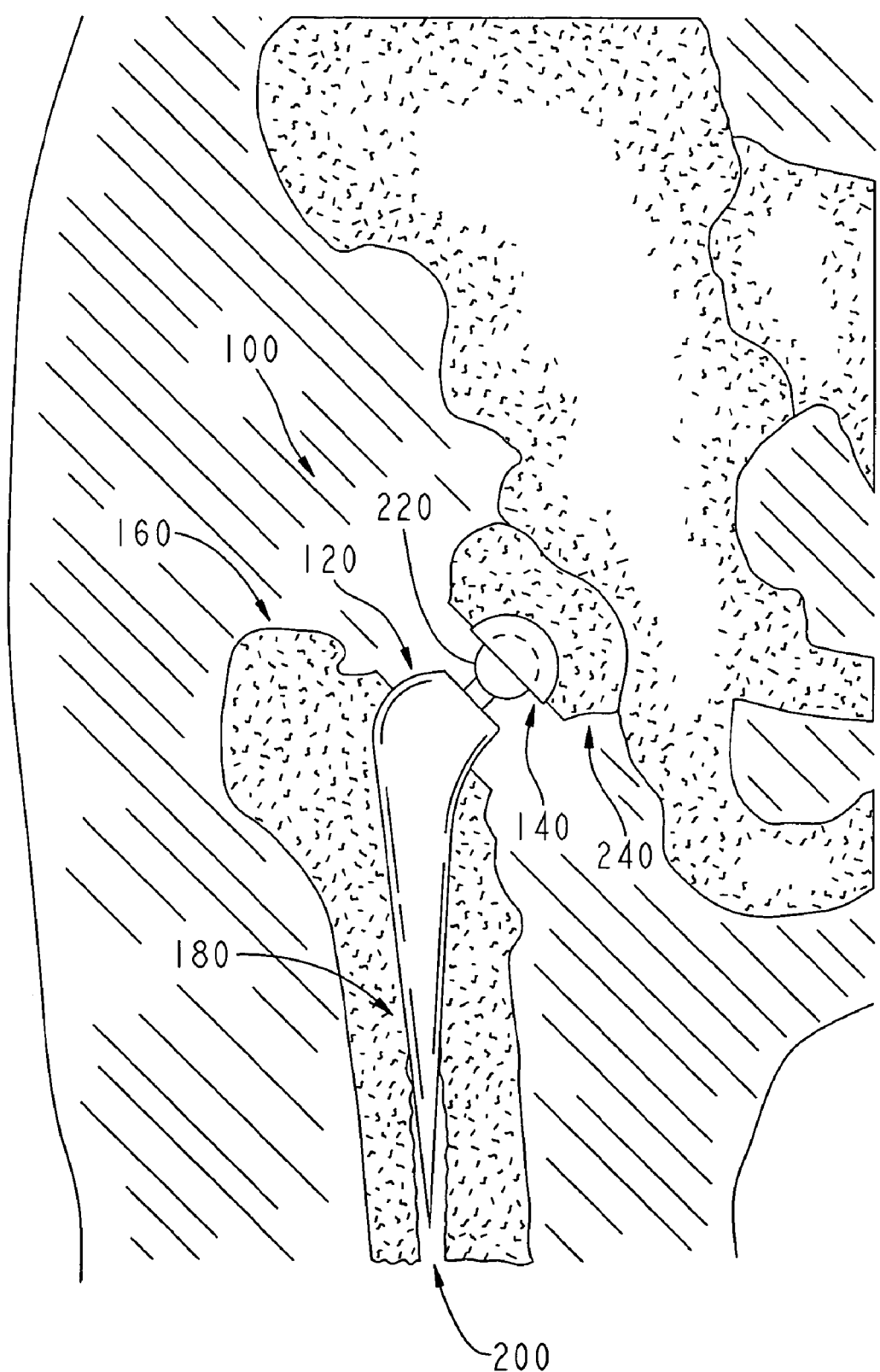
FIG. 1 shows an exemplary hip prosthesis including an exemplary femoral implant and further including an exemplary acetabular implant according to the present invention.

Like reference numerals refer to like parts throughout the following description and the accompanying drawings. As used herein, the terms "medial," "medially," and the like mean pertaining to the middle, in or toward the middle, and/or nearer to the middle of the body when standing upright. Conversely, the terms "lateral," "laterally," and the like are used herein as opposed to medial. For example, the medial side of the knee is the side closest to the other knee and the closest sides of the knees are medially facing, whereas the lateral side of the knee is the outside of the knee and is laterally facing. Further, as used herein the term "superior" means closer to the top of the head and/or farther from the bottom of the feet when standing upright. Conversely, the term "inferior" is used herein as opposed to superior. For example, the heart is superior to the stomach and the superior surface of the tongue rests against the palate, whereas the stomach is inferior to the heart and the palate faces inferiorly toward the tongue. Also, as used herein the terms "anterior," "anteriorly," and the like mean nearer the front or facing away from the front of the body when standing upright, as opposed to "posterior," "posteriorly," and the like, which mean nearer the back or facing away from the back of the body. Additionally, as used herein the term "generally hemispherical" is intended its broadest sense to encompass all concave and convex geometries suitable for applicable components of prosthetic ball-and-socket type joints such as acetabular and glenoid shells, integuments, bearings, and the like, and, accordingly, includes hemispherical geometries, includes partially spherical geometries that are more than hemispherical, includes partially spherical geometries that are less than hemispherical, and includes all suitable curved polygonal and geodesic geometries as well. Further, as used herein the terminology "taper couple" and inflections thereof mean to fasten together via a taper joint. In general, a taper joint or taper coupling is formed by pressing together ("press-fitting") a male part ("male taper") and a female part ("female taper") having impinging angled or flared surfaces. Taper couplings are generally known in the art. For example, the disclosure of U.S. Pat. No. 6,610,097 to Serbousek et al, which is expressly incorporated herein by reference, discusses manners of making and using various taper couplings that may be suitable for incorporation into applicable embodiments of the present invention.

FIG. 1 shows an exemplary hip prosthesis 100 including an exemplary femoral implant 120 and further including an exemplary acetabular implant 140 according to the present invention. Among other things, implant 120 is configured as known to replace natural hip components (not shown) of a distal femur 160. In the exemplary embodiment, implant 120 is metallic and preferably made from titanium. In alternative embodiments, implant 120 may be made from a cobalt chrome alloy or any other suitable biocompatible material(s). Implant 120 includes a post 180. Among other things, post 180 is configured as known to anchor into a medullary canal 200 of distal femur 160. Implant 120 also includes a substantially spherical ball 220. Among other things, implant 140 is configured to replace natural hip components (not shown) of an acetabulum 240. Accordingly, implant 140 defines a generally hemispherical artificial hip socket 260 (see FIG. 2 and FIG. 5) that receives ball 220 as known such that ball 220 has suitable pivotal freedom within socket 260. Implant 140 is discussed further below.

Figure 2:
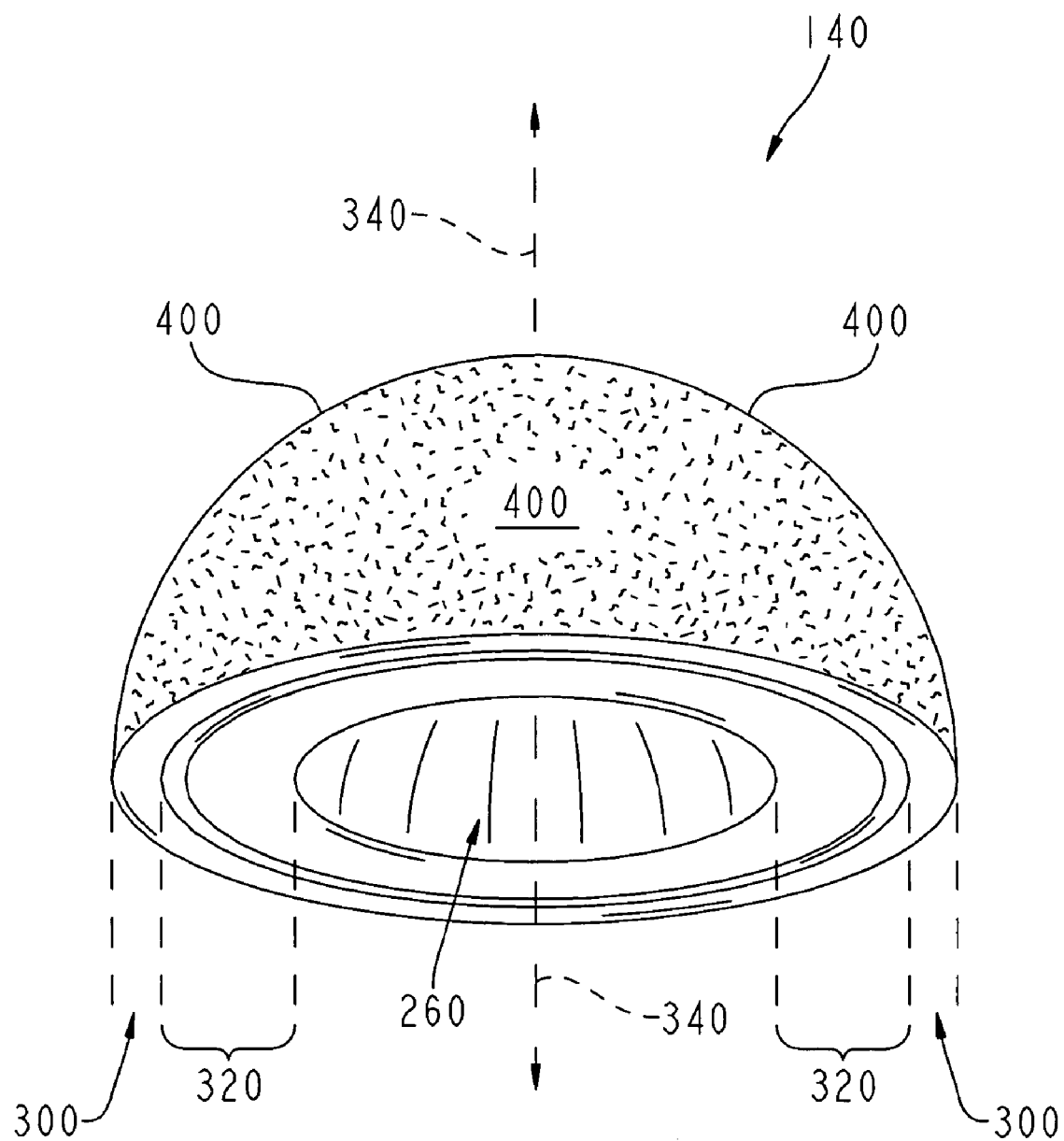
FIG. 2 shows a perspective view of the exemplary acetabular implant of FIG. 1.

FIG. 2 shows a perspective view of exemplary implant 140. Implant 140 includes a dome-like or cup-like acetabular shell 300, and a dome-like or cup-like metal-backed bearing sub-assembly 320 (see also FIG. 3). Among other things, shell 300 is configured to be anchored into acetabulum 240 (see FIG. 1) in a known manner, and is configured to taper couple to sub-assembly 320 in accordance with the exemplary embodiment. In the exemplary embodiment, shell 300 is metallic and preferably made from titanium. In alternative embodiments, shell 300 may be made from a cobalt chrome alloy or any other suitable biocompatible material(s). Further, shell 300 is symmetrical about an axis 340 and includes a generally concave inner surface 360 (see FIG. 4) defining a generally concave cavity or socket 380 (see FIG. 4) that is symmetrical about axis 340. Further, shell 300 includes a generally hemispherical outer surface 400 facing generally outwardly away from socket 380. In the exemplary embodiment, surface 400 is suitably textured as known to facilitate fixation in acetabulum 240. Additionally, it is noted that surface 400 may be suitably covered with a porous material (not shown) as known to enhance acetabular fixation of shell 300 through bone in growth.

Figure 3:
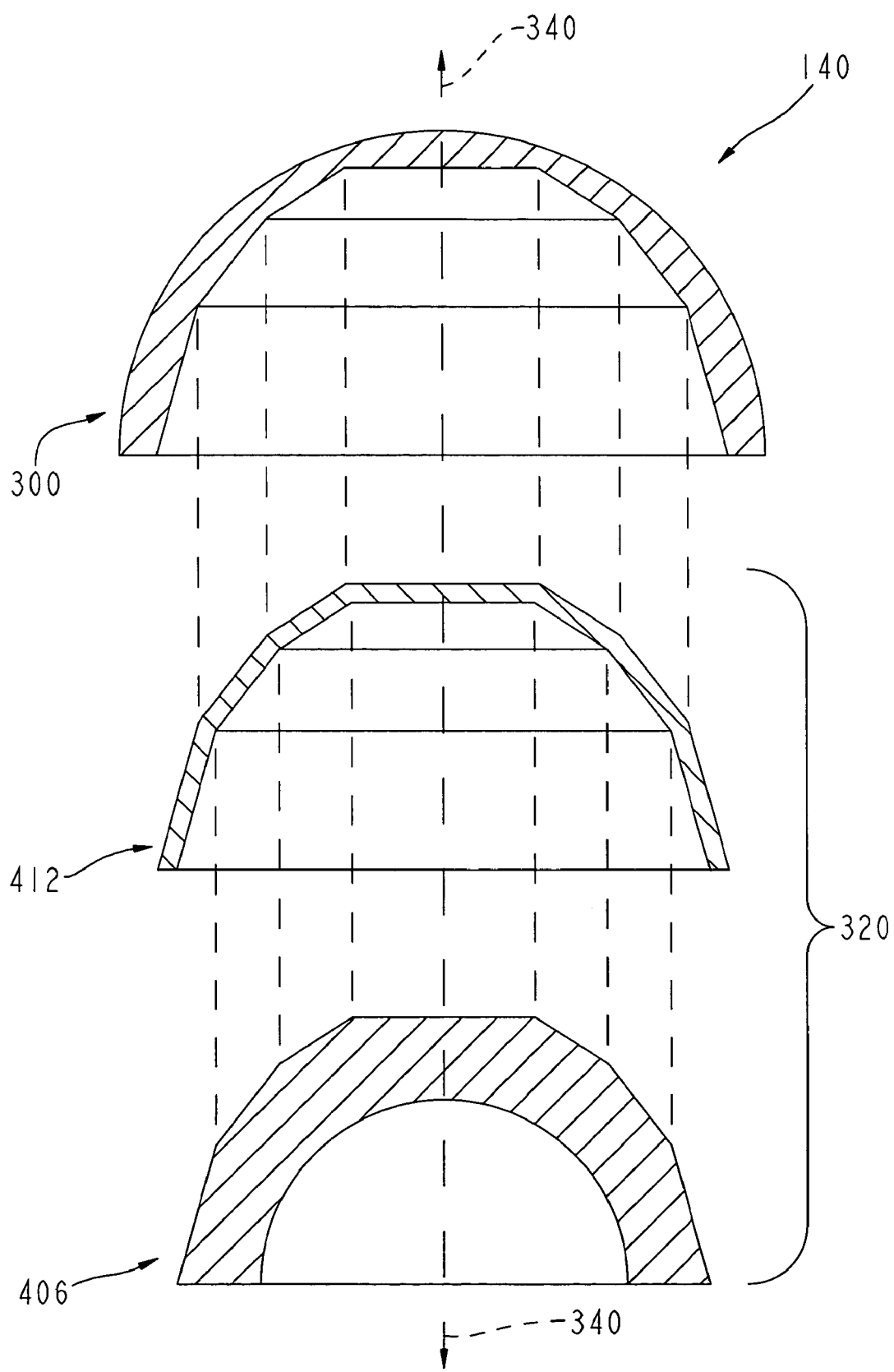
FIG. 3 shows an exploded axial cross-sectional view of the exemplary acetabular implant of FIG. 1.

FIG. 3 shows an exploded axial cross-sectional view of implant 140. As at least partially discernable in FIG. 3, sub-assembly 320 includes a dome-like or cup like bearing 406 and a dome-like or cup-like backing or integument 412. Shell 300 and axis 340, among other things, are also at least partially discernable in FIG. 3. Bearing 406 and integument 412 are discussed further below.

Figure 4:
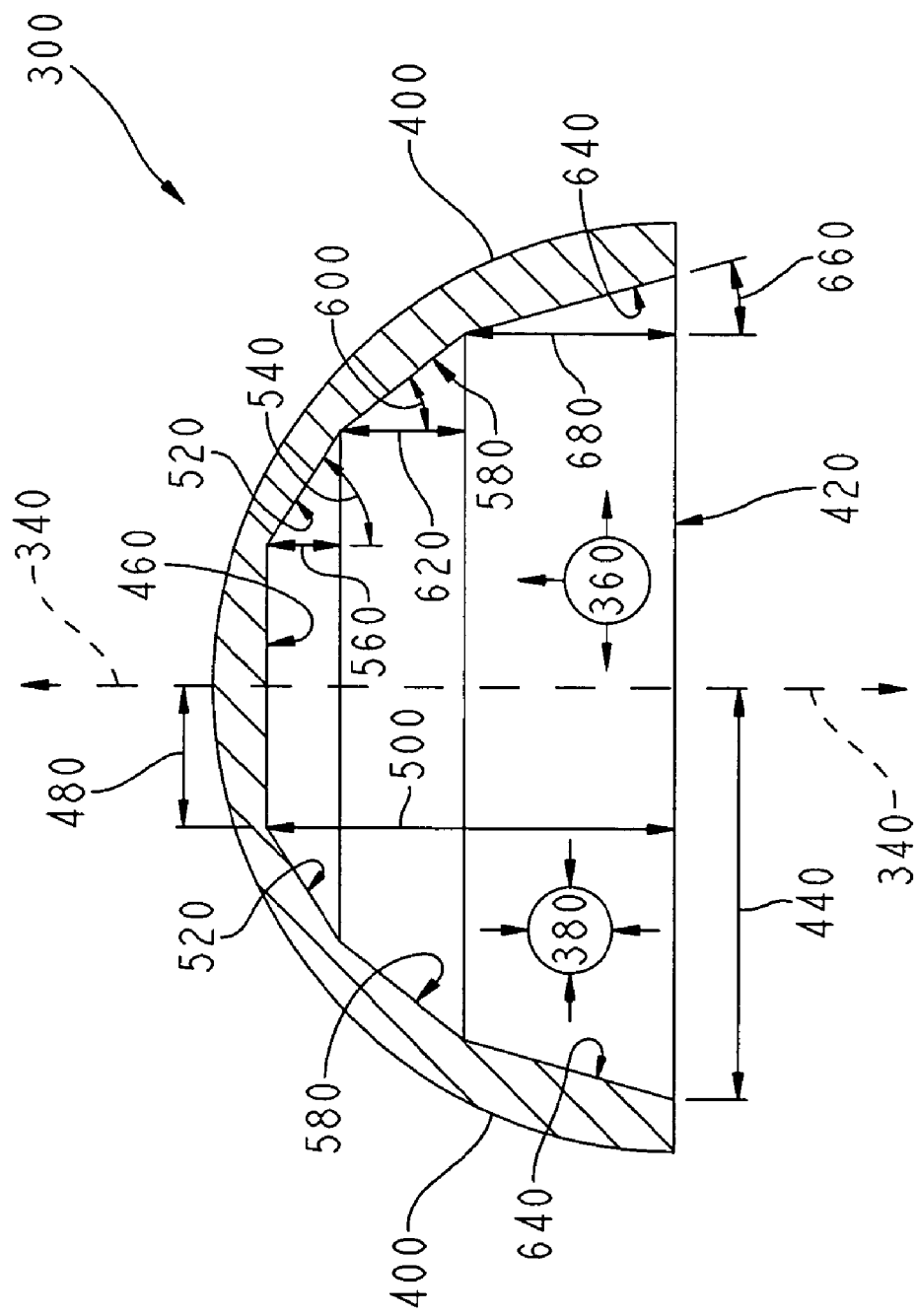
FIG. 4 shows an axial cross-sectional view the shell of the exemplary acetabular implant of FIG. 1.

FIG. 4 shows an axial cross-sectional view of shell 300. As at least partially discernable in FIG. 4, surface 360 of shell 300 includes an annular rim 420 centered about axis 340 with a radius 440. Surface 360 also includes a circular flat 460 centered about axis 340 with a radius 480. Flat 460 is disposed from rim 420 by an axial dimension 500. Socket 380 opens at rim 420, while flat 460 bounds socket 380 axially inwardly from rim 420. Further, surface 360 defines an annular female taper 520 extending from flat 460 generally towards rim 420 at a taper angle 540 relative to axis 340. Axially, taper 520 extends from flat 460 by a dimension 560. Surface 360 also defines an annular female taper 580 extending from taper 520 generally towards rim 420 at a taper angle 600 relative to axis 340. Axially, taper 580 extends from taper 520 by a dimension 620. Surface 360 also defines an annular female taper 640 extending from taper 580 generally towards rim 420 at a taper angle 660 relative to axis 340. Axially, taper 640 extends from taper 580 by a dimension 680. In the exemplary embodiment, radius 480 is less than radius 440, angle 600 is less than angle 540, and angle 660 is less than angle 600, while dimension 620 is greater than dimension 560, and dimension 680 is greater than dimension 620.

Figure 5:
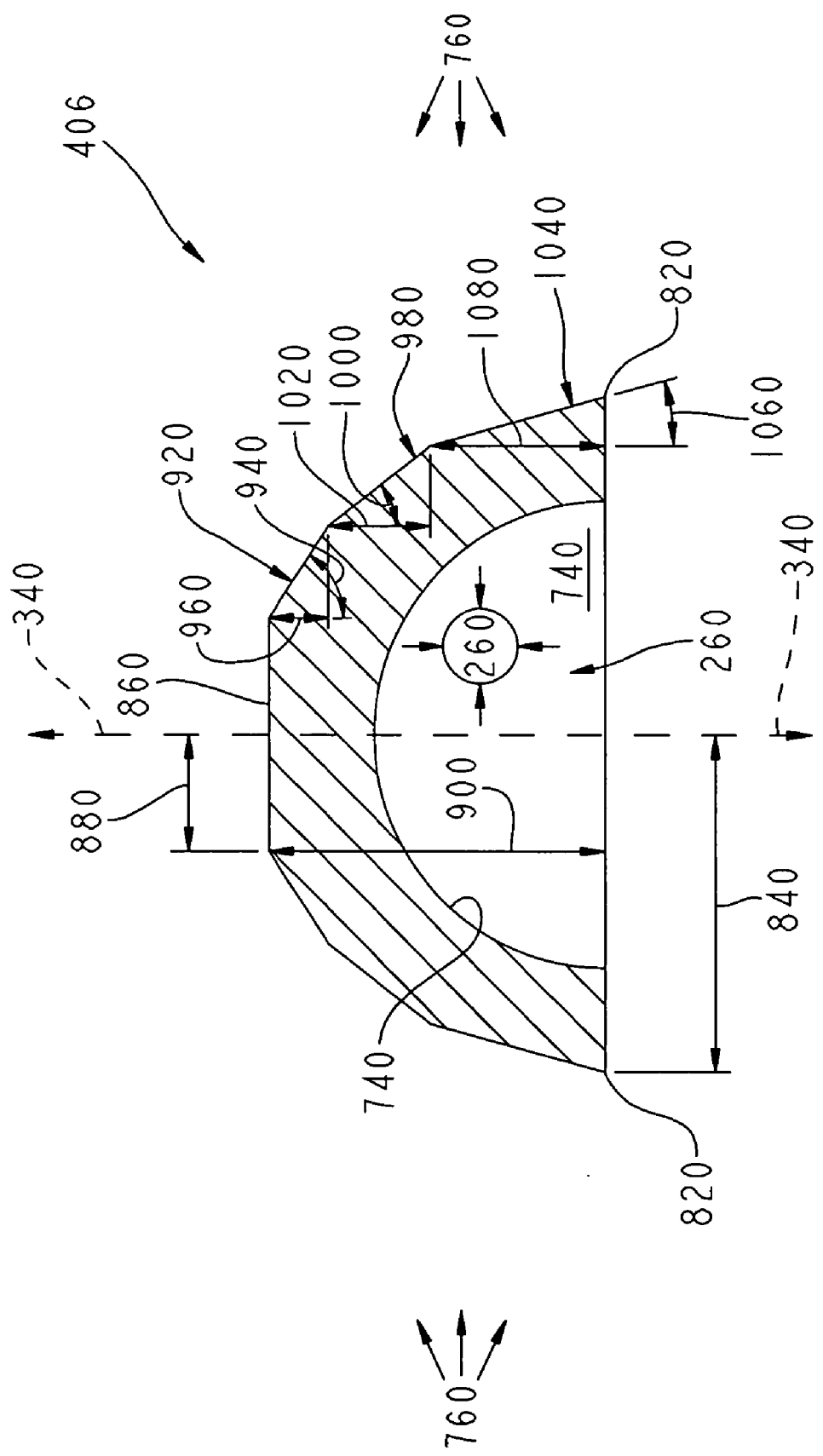
FIG. 5 shows an axial cross-sectional view the bearing of the exemplary acetabular implant of FIG. 1.

FIG. 5 shows an axial cross-sectional view of bearing 406. Among other things, bearing 406 is configured as known to receive ball 220 (see FIG. 1) in socket 260 and is configured to couple into integument 412 according to the exemplary embodiment of the present invention. In the exemplary embodiment, bearing 406 is made from a plastic, preferably ultra high molecular weight polyethylene ("UHMWPE"). In alternative embodiments, bearing 406 may be made from any other suitable biocompatible material(s). As at least partially discernable in FIG. 5, bearing 406 includes a generally hemispherical and generally concave inner surface 740 that is suitably machined as known to define socket 260. Bearing 406 also includes a generally convex outer surface 760 that faces generally outwardly away from socket 260. Surface 760 includes an annular rim 820 centered about axis 340 with a radius 840. Surface 760 also includes a circular flat 860 centered about axis 340 with a radius 880. Flat 860 is disposed from rim 820 by an axial dimension 900. Further, surface 760 defines an annular male taper 920 extending from flat 860 generally towards rim 820 at a taper angle 940 relative to axis 340. Axially, taper 920 extends from flat 860 by a dimension 960. Surface 760 also defines an annular male taper 980 extending from taper 920 generally towards rim 820 at a taper angle 1000 relative to axis 340. Axially, taper 980 extends from taper 920 by a dimension 1020. Surface 760 also defines an annular male taper 1040 extending from taper 980 generally towards rim 820 at a taper angle 1060 relative to axis 340. Axially, taper 1040 extends from taper 980 by a dimension 1080. In the exemplary embodiment, radius 880 is less than radius 840, angle 1000 is less than angle 940, and angle 1060 is less than angle 1000, while dimension 1020 is greater than dimension 960, and dimension 1080 is greater than dimension 1020.

Figure 6:
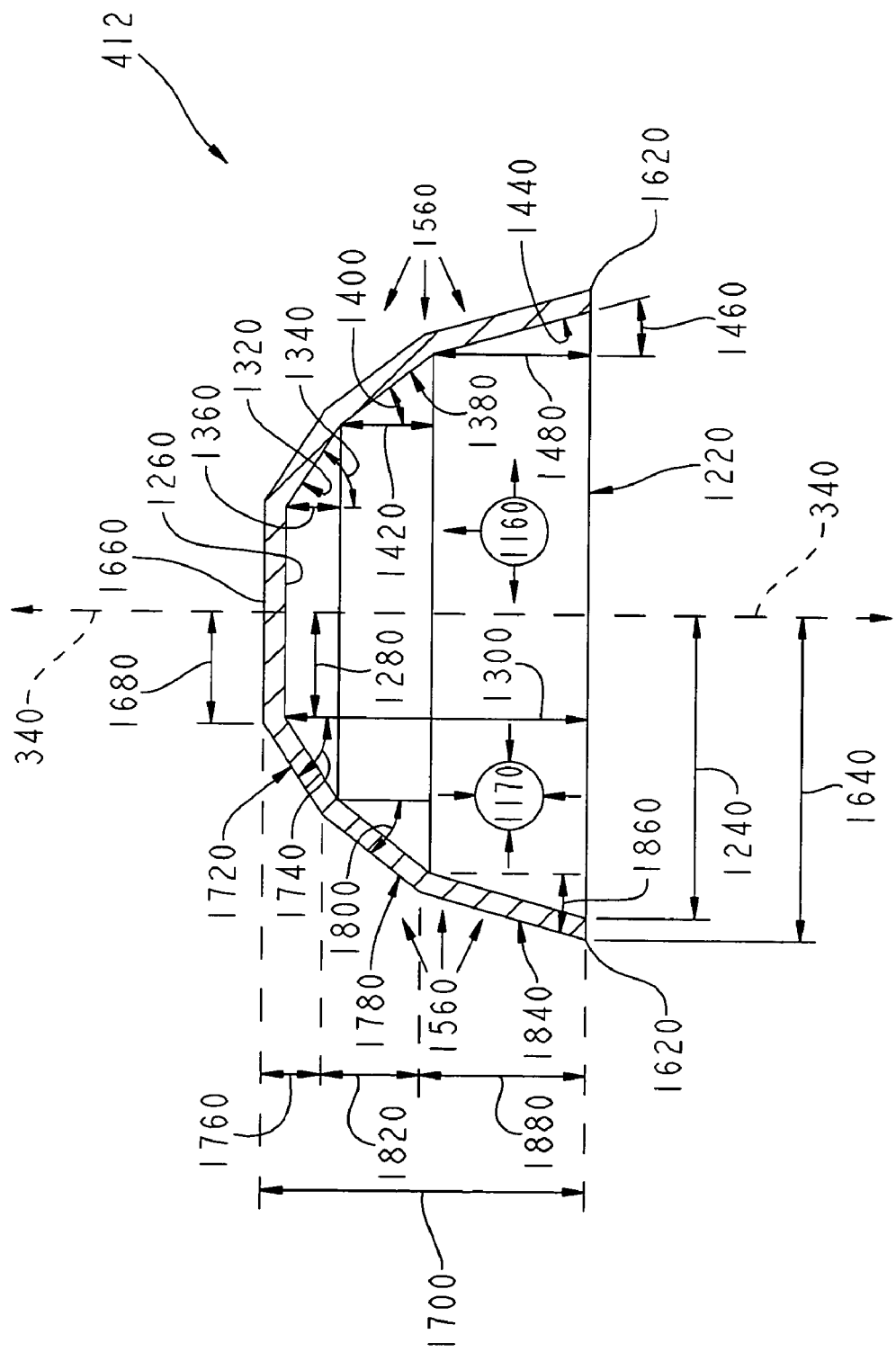
FIG. 6 shows an axial cross-sectional view of the integument of the exemplary acetabular implant of FIG. 1.

FIG. 6 shows an axial cross-sectional view of integument 412. Among other things, integument 412 is configured to couple around bearing 406 and to couple into shell 300 according to the exemplary embodiment of the present invention. In the exemplary embodiment, integument 412 is metallic and preferably made from titanium. In alternative embodiments, integument 412 may be made from a cobalt chrome alloy or any other suitable biocompatible material(s). As at least partially discernable in FIG. 6, integument 412 includes a generally concave inner surface 1160 that defines a generally concave socket 1170. Surface 1160 includes an annular rim 1220 centered about axis 340 with a radius 1240. Surface 1160 also includes a circular flat 1260 centered about axis 340 with a radius 1280. Flat 1260 is disposed from rim 1220 by an axial dimension 1300. Further, surface 1160 defines an annular female taper 1320 extending from flat 1260 generally towards rim 1220 at a taper angle 1340 relative to axis 340. Axially, taper 1320 extends from flat 1260 by a dimension 1360. Radius 1280, angle 1340 and dimension 1360 are sized such that taper 1320 securely taper couples to taper 920 (of bearing 406; see FIG. 5) upon assembly of sub-assembly 320 (see FIG. 3). Surface 1160 also defines an annular female taper 1380 extending from taper 1320 generally towards rim 1220 at a taper angle 1400 relative to axis 340. Axially, taper 1380 extends from taper 1320 by a dimension 1420. Angle 1400 and dimension 1420 are sized such that taper 1380 securely taper couples to taper 980 (of bearing 406; see FIG. 5) upon assembly of sub-assembly 320 (see FIG. 3). Surface 1160 also defines an annular female taper 1440 extending from taper 1380 generally towards rim 1220 at a taper angle 1460 relative to axis 340. Axially, taper 1440 extends from taper 1380 by a dimension 1480. Angle 1460 and dimension 1480 are sized such that taper 1440 securely taper couples to taper 1040 (of bearing 406; see FIG. 5) upon assembly of sub-assembly 320 (see FIG. 3). In the exemplary embodiment, dimension 1300 is about equal to dimension 900 (of bearing 406; see FIG. 5), radius 1280 is less than radius 1240, angle 1400 is less than angle 1340, and angle 1460 is less than angle 1400, while dimension 1420 is greater than dimension 1360, and dimension 1480 is greater than dimension 1420.

Integument 412 also includes a generally convex outer surface 1560 that faces generally outwardly away from socket 1170. Surface 1560 includes an annular rim 1620 centered about axis 340 with a radius 1640. Surface 1560 also includes a circular flat 1660 centered about axis 340 with a radius 1680. Flat 1660 is disposed from rim 1620 by an axial dimension 1700. Further, surface 1560 defines an annular male taper 1720 extending from flat 1660 generally towards rim 1620 at a taper angle 1740 relative to axis 340. Axially, taper 1720 extends from flat 1660 by a dimension 1760. Radius 1680, angle 1740 and dimension 1760 are sized such that taper 1720 and flat 1660 have clearance with flat 460 and taper 520 upon assembly of implant 140. Surface 1560 also defines an annular male taper 1780 extending from taper 1720 generally towards rim 1620 at a taper angle 1800 relative to axis 340. Axially, taper 1780 extends from taper 1720 by a dimension 1820. Angle 1800 and dimension 1820 are sized such that taper 1780 has clearance with taper 580 upon assembly of implant 140. Surface 1560 also defines an annular male taper 1840 extending from taper 1780 generally towards rim 1620 at a taper angle 1860 relative to axis 340. Axially, taper 1840 extends from taper 1780 by a dimension 1880. Angle 1860 and dimension 1880 are sized such that taper 1840 securely taper couples to taper 640 (of shell 300; see FIG. 4) upon assembly of implant 140 (see FIG. 3). In the exemplary embodiment, dimension 1700 is less than dimension 500 (of shell 300; see FIG. 4), radius 1680 is less than radius 1640, angle 1800 is less than angle 1740, and angle 1860 is less than angle 1800, while dimension 1820 is greater than dimension 1760, and dimension 1880 is greater than dimension 1820.

To begin assembly of implant 140, bearing 406 is press-fitted axially into socket 1170 (of integument 412) to assemble or unite sub-assembly 320. Here, it is noted that although implant 140 is fully exploded in FIG. 3 for clarity of exposition, bearing 406 is preferably pre-operatively press-fitted into socket 1170 by a manufacturer to unite sub-assembly 320 separately from shell 300. Such pre-operative unification of sub-assembly 320 may include temporarily cooling bearing 406 (by immersing it in liquid nitrogen or by any other suitable refrigeration method(s)) immediately prior to press-fitting it into socket 1170, followed by allowing bearing 406 to warm or reheat to a normal temperature (and thus un-shrink or re-expand) within socket 1170 so as to additionally tighten bearing 406 within socket 1170. Upon unification of sub-assembly 320, taper 1040 taper couples to taper 1440, which taper couples surface 760 to surface 1160, and, thus, taper couples bearing 406 to integument 412. It is noted that the strength of the taper coupling reduces or eliminates needs for additional undesirably complex and/or costly structures that might otherwise be required to prevent dislocation and/or rotation of bearing 406 within integument 412.

Assembly of implant 140 is completed by suitably rotationally aligning sub-assembly 320 relative to shell 300 about axis 340 and then press-fitting sub-assembly 320 axially into socket 380 (of shell 300). Here, it is noted that the annular designs of taper 1720, taper 520, taper 1780, taper 580, taper 1840, and taper 640 allow for infinite rotational orientation or alignment of sub-assembly 320 (including bearing 406 and, thus, socket 260 as well) prior to press-fitting sub-assembly 320 into socket 380. Such infinite rotational resolution may be especially advantageous for alternative embodiments of the present invention in which socket 260 is off-centered from axis 340. Upon press-fitting sub-assembly 320 into socket 380, taper 1840 taper couples to taper 640, which taper couples surface 1560 to surface 360, and, thus, taper couples integument 412 (and thus, sub-assembly 320) to shell 300. It is noted that the strength of the taper coupling reduces or eliminates needs for additional undesirably complex and/or costly structures that might otherwise be required to prevent dislocation and/or rotation of sub-assembly 320 within shell 300.

To assemble prosthesis 100, distal femur 160 and acetabulum 240 are suitably resected, post 180 is suitably anchored into medullary canal 200, and shell 300 is suitably anchored into acetabulum 240. Sub-assembly 320 is rotationally aligned relative to shell 300 and then press-fitted into socket 380. Lastly, ball 220 is inserted into socket 260.

In operation of prosthesis 100, bearing 406 stays taper coupled to integument 412 within socket 1170; sub-assembly 320 (including bearing 406 and integument 412) stays taper coupled to shell 300 within socket 380; and pivotal freedom of ball 220 within socket 260 allows articulation of implant 120 relative to implant 140.

Figure 7:
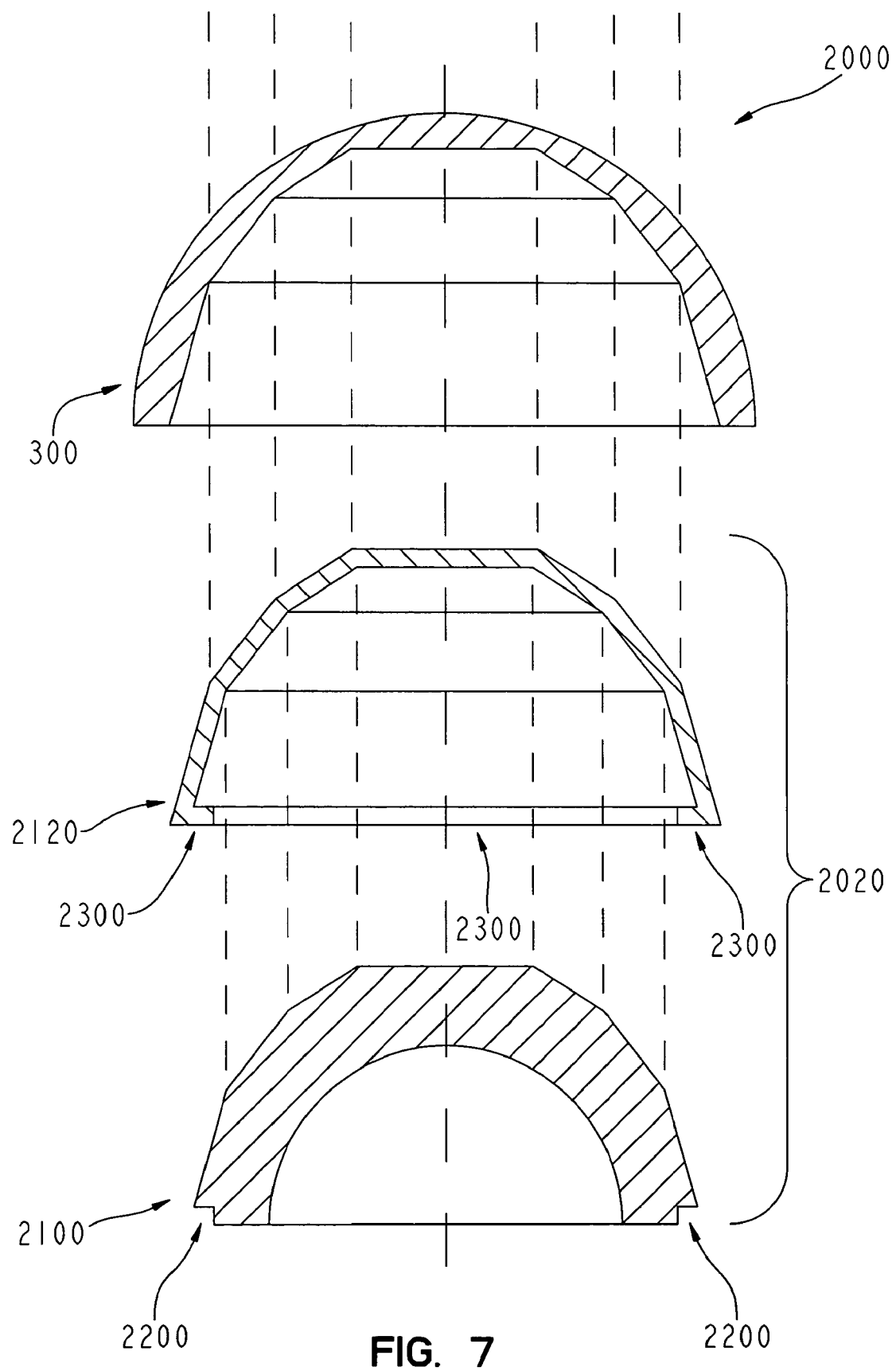
FIG. 7 shows an exploded axial cross-sectional view of an exemplary alternative acetabular implant according to the present invention.

FIG. 7 shows an exploded axial cross-sectional view of an exemplary alternative acetabular implant 2000 according to the present invention. Implant 2000 is made and used in a like manner to implant 140 (discussed above) except that sub-assembly 320 is replaced with an alternative dome-like or cup-like metal-backed bearing sub-assembly 2020. Sub-assembly 2020 includes an alternative dome-like or cup like bearing 2100 and an alternative dome-like or cup-like backing or integument 2120. Bearing 2100 is made and used in a like manner to bearing 406 except that rim 820 is replaced with a radially inwardly extending annular ledge 2200. Integument 2120 is made and used in a similar manner to integument 412 except that rim 1220 is replaced with a radially inwardly extending annular flange 2300. When sub-assembly 2020 is united, flange 2300 abuts ledge 2200 to additionally inhibit dislocation and/or rotation of bearing 2100 within integument 2120.

Figure 8:
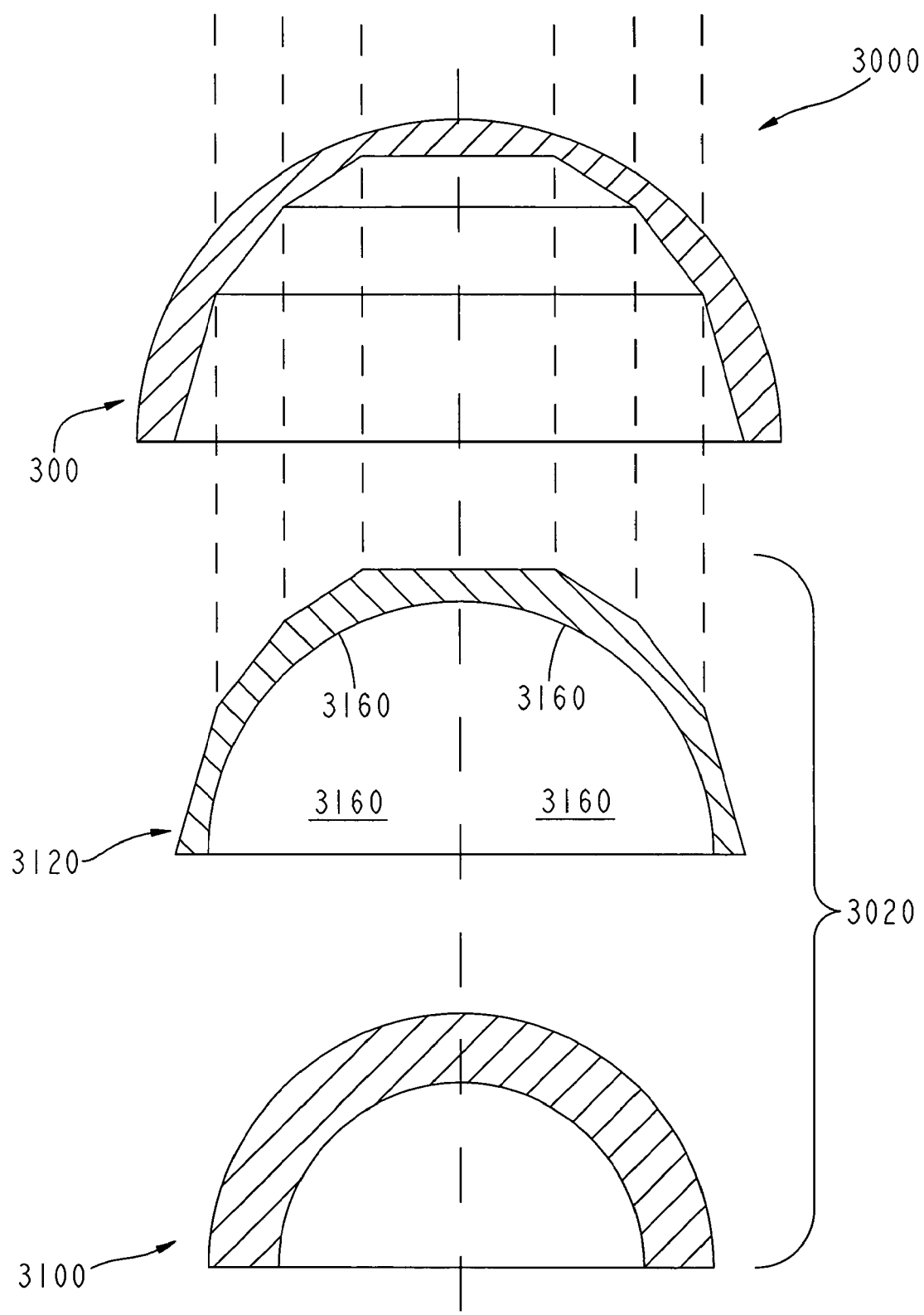
FIG. 8 shows an exploded axial cross-sectional view of another exemplary alternative acetabular implant according to the present invention.

FIG. 8 shows an exploded axial cross-sectional view of another exemplary alternative acetabular implant 3000 according to the present invention. Implant 3000 is made and used in a like manner to implant 140 (discussed above) except that sub-assembly 320 is replaced with an alternative dome-like or cup-like metal-backed bearing sub-assembly 3020. Sub-assembly 3020 includes an alternative dome-like or cup like bearing 3100 and an alternative dome-like or cup-like backing or integument 3120. Bearing 3100 and integument 3120 are made and used in similar manners to bearing 406 and integument 412, respectively, except that bearing 3100 and integument 3120 are not taper coupled to each other; instead, surface 1160 is replaced with a generally hemispherical generally concave surface 3160, and bearing 3100 is compression molded directly onto surface 3160. Further, prior to compression molding bearing 3100 onto surface 3160, surface 3160 is preferably roughened to produce a more adherent substrate. The roughening is preferably accomplished by dry blasting surface 3160 with 60 grit alumina, or, in alternative embodiments, via any other suitable method.

The foregoing description of the invention is illustrative only, and is not intended to limit the scope of the invention to the precise terms set forth. Further, although the invention has been described in detail with reference to certain illustrative embodiments, variations and modifications exist within the scope and spirit of the invention as described and defined in the following claims.

What is claimed is:

1. An acetabular implant comprising:
   a longitudinal axis;
   a shell having an outer shell surface and an inner shell surface, the outer shell surface configured to contact bone;
   an integument having an outer integument surface and an inner integument surface, the outer integument surface configured to couple to the inner shell surface; and
   a plastic bearing having an outer bearing surface and an inner bearing surface, the inner bearing surface defining a socket, the inner integument surface configured to form a friction-fit with the outer bearing surface;
   wherein the inner integument surface comprises a base centered about the longitudinal axis and extending substantially perpendicular to the longitudinal axis; and
   wherein the inner integument surface further comprises a first taper portion and a second taper portion, the first taper portion extending a first distance from the base of the integument and the second taper portion extending a second distance from the first taper portion, the second distance exceeding the first distance.

2. The acetabular implant of claim 1, wherein the plastic bearing comprises ultra high molecular weight polyethylene.

3. The acetabular implant of claim 1, wherein the inner integument surface defines an annular female taper and the outer bearing surface defines an annular male taper configured to taper couple to the annular female taper of the inner integument surface.

4. The acetabular implant of claim 1, wherein the outer bearing surface comprises a second base centered about the longitudinal axis and extending substantially perpendicular to the longitudinal axis, the second base of the bearing sized to engage the base of the integument.

5. The acetabular implant of claim 1, wherein the inner integument surface further comprises a first taper portion and a second taper portion, the first taper portion extending from the base of the integument at a first angle relative to the longitudinal axis and the second taper portion extending from the first taper portion at a second angle relative to the longitudinal axis, the first angle exceeding the second angle.

6. The acetabular implant of claim 1, further comprising a longitudinal axis, wherein the integument includes an annular rim and the inner integument surface includes a first taper portion and a second taper portion, the first taper portion extending from the annular rim at a first angle relative to the longitudinal axis and the second taper portion extending from the first taper portion at a second angle relative to the longitudinal axis, the second angle exceeding the first angle.

7. The acetabular implant of claim 1, wherein the integument includes an annular rim and the inner integument surface includes a first taper portion and a second taper portion, the first taper portion extending a first distance from the annular rim and the second taper portion extending a second distance from the first taper portion, the first distance exceeding the second distance.

8. The acetabular implant of claim 1, wherein the inner shell surface defines an annular female taper and the outer integument surface defines an annular male taper configured to taper couple to the annular female taper of the inner shell surface.

9. The acetabular implant of claim 1, wherein:
   the integument comprises a first annular rim having a flange that projects from the first annular rim; and
   the bearing comprises a second annular rim having a groove configured to receive the flange of the integument.

10. An acetabular implant comprising:
    a longitudinal axis;
    a shell configured to contact bone;
    a plastic bearing defining a socket; and
    an integument positionable between the shell and the bearing, the integument configured to form a friction-fit with the bearing;
    wherein the integument comprises a base centered about the longitudinal axis and extending substantially perpendicular to the longitudinal axis; and
    wherein the integument further comprises a first taper portion and a second taper portion, the first taper portion extending a first distance from the base of the integument and the second taper portion extending a second distance from the first taper portion, the second distance exceeding the first distance.

11. The acetabular implant of claim 10, wherein the plastic bearing comprises ultra high molecular weight polyethylene.

12. The acetabular implant of claim 10, wherein the bearing defines an annular male taper and the integument defines an annular female taper configured to taper couple to the annular male taper of the bearing.

13. The acetabular implant of claim 10, wherein the bearing comprises a second base centered about the longitudinal axis and extending substantially perpendicular to the longitudinal axis, the second base of the bearing sized to engage the base of the integument.

14. The acetabular implant of claim 10, wherein the integument further comprises a first taper portion and a second taper portion, the first taper portion extending from the base of the integument at a first angle relative to the longitudinal axis and the second taper portion extending from the first taper portion at a second angle relative to the longitudinal axis, the first angle exceeding the second angle.

15. The acetabular implant of claim 10, further comprising a longitudinal axis, wherein the integument includes an annular rim, a first taper portion, and a second taper portion, the first taper portion extending from the annular rim at a first angle relative to the longitudinal axis and the second taper portion extending from the first taper portion at a second angle relative to the longitudinal axis, the second angle exceeding the first angle.

16. The acetabular implant of claim 10, wherein the integument includes an annular rim, a first taper portion, and a second taper portion, the first taper portion extending a first distance from the annular rim and the second taper portion extending a second distance from the first taper portion, the first distance exceeding the second distance.

17. The acetabular implant of claim 10, wherein the shell defines an annular female taper and the integument defines an annular male taper configured to taper couple to the annular female taper of the shell.

18. The acetabular implant of claim 10, wherein:
the integument comprises a first annular rim having a flange that projects from the first annular rim; and
the bearing comprises a second annular rim having a groove configured to receive the flange of the integument.

* * * * *